United States Patent [19]

Grinder

[11] Patent Number: 4,562,599
[45] Date of Patent: * Jan. 7, 1986

[54] INTRAOCULAR LENS

[75] Inventor: William H. Grinder, San Francisco, Calif.

[73] Assignee: Minnesota Mining and Manufacturing Company, Saint Paul, Minn.

[*] Notice: The portion of the term of this patent subsequent to Oct. 2, 2001 has been disclaimed.

[21] Appl. No.: 630,268

[22] Filed: Aug. 22, 1984

Related U.S. Application Data

[63] Continuation of Ser. No. 489,778, Jun. 2, 1983, Pat. No. 4,473,910, which is a continuation of Ser. No. 312,272, Oct. 16, 1981, abandoned, which is a continuation of Ser. No. 113,682, Jan. 21, 1980, abandoned.

[51] Int. Cl.[4] .............................. A61F 1/16; A61F 1/24
[52] U.S. Cl. ............................................................. 623/6
[58] Field of Search ............................................. 3/13, 1

[56] References Cited

U.S. PATENT DOCUMENTS

| | | |
|---|---|---|
| 2,834,023 | 5/1958 | Lieb ........................................ 3/1 |
| 4,014,049 | 3/1977 | Richards et al. ...................... 3/13 |
| 4,056,855 | 11/1977 | Kelman ................................. 3/13 |
| 4,077,071 | 3/1978 | Freeman ............................... 3/13 |
| 4,092,743 | 6/1978 | Kelman ................................. 3/13 |
| 4,110,848 | 9/1978 | Jensen .................................. 3/13 |
| 4,159,546 | 7/1979 | Shearing ............................... 3/13 |
| 4,174,543 | 11/1979 | Kelman ................................. 3/13 |
| 4,251,887 | 2/1981 | Anis ...................................... 3/13 |
| 4,254,510 | 3/1981 | Tennant ................................ 3/13 |
| 4,328,595 | 5/1982 | Sheets ................................... 3/13 |

FOREIGN PATENT DOCUMENTS

| | | | |
|---|---|---|---|
| 2717706 | 10/1978 | Fed. Rep. of Germany ............ 3/13 |
| 7616918 | 12/1976 | France ................................. 3/13 |
| 1511966 | 5/1978 | United Kingdom .................... 3/13 |
| 1545252 | 5/1979 | United Kingdom .................... 3/13 |
| 2046099 | 11/1980 | United Kingdom .................... 3/13 |
| 2057270 | 4/1981 | United Kingdom .................... 3/13 |
| 563174 | 6/1977 | U.S.S.R. ............................... 3/13 |

OTHER PUBLICATIONS

"Covered Bridge, an Update on Lens Implantation", or Bridge Over Troubled Waters, (3rd Attempt), (Book), by Dr. John Sheets, 1977, pp. 5–13.

"The Intraocular Lens Manual," a copendium by Dennis D. Sheperd, M.D.

"The Intraocular Implant Lens," by M. E. Nordlohne, M.D. (Book), The Williams & Wilkens Co., Baltimore, 1975.

Primary Examiner—Ronald L. Frinks
Attorney, Agent, or Firm—Donald M. Sell; James A. Smith; Jennie G. Boeder

[57] ABSTRACT

An intraocular lens for positioning in the posterior chamber of the eye having a plastic lens body supported by first and second resilient spring-like support loops extending from opposite sides of the peripheral edge of the lens body; in use the support loop is preferably resiliently compressed against the equatorial region of the lens capsule of the eye from which the natural lens has been removed.

24 Claims, 4 Drawing Figures

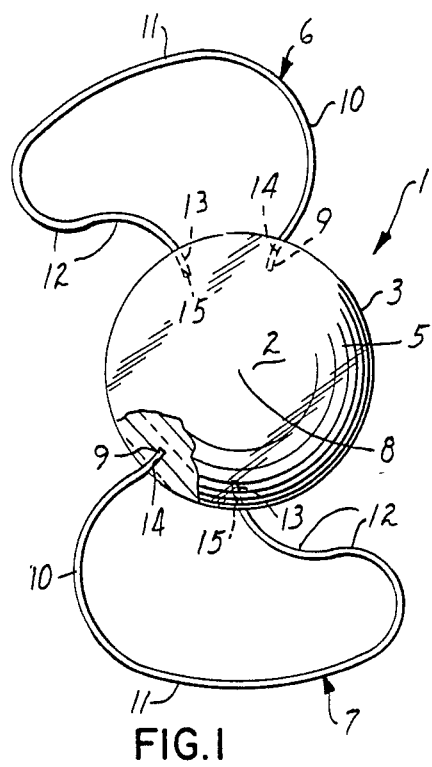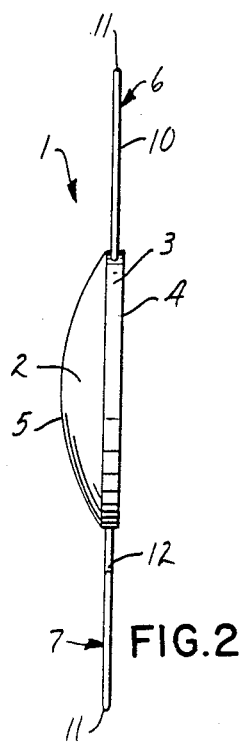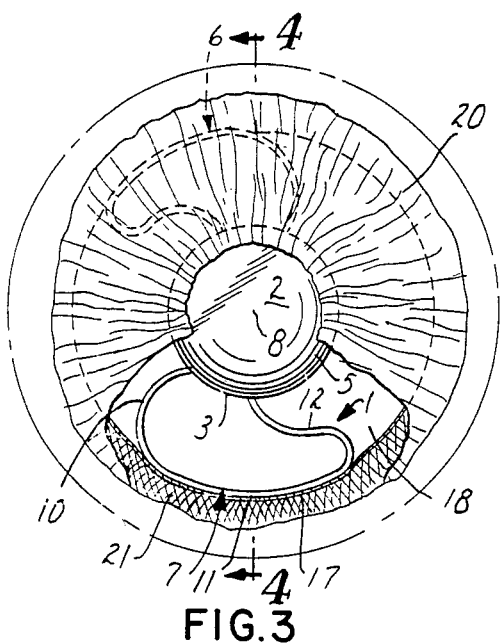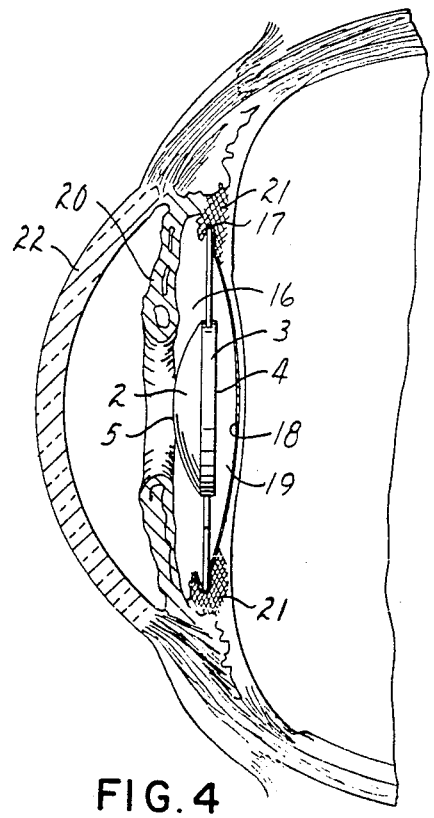

INTRAOCULAR LENS

This is a continuation of application Ser. No. 489,778, filed June 2, 1983, now U.S. Pat. No. 4,473,910; which is a continuation of Ser. No. 312,272, filed Oct. 16, 1981, now abandoned; which is a continuation of U.S. Ser. No. 113,682, filed Jan. 21, 1980, now abandoned.

This invention relates to intraocular lenses. Particularly, this invention relates to an intraocular lens for implantation in the posterior chamber of the human eye having at least one resilient spring-like support loop holding the lens in the lens capsule of the posterior chamber of the human eye.

Intraocular lens implantation after cataract surgery has come into common usage because of the improved vision obtained thereby over the alternatives of contact lenses or spectacles. Intraocular lenses have been implanted in both the posterior as well as the anterior chamber of the eye. The first intraocular lens apparently implanted was by Dr. Harold Ridley in 1949. This lens was implanted in the posterior chamber and was implanted following extra-capsular cataract extraction. However, due to a large number of complications, this procedure did not result in wide acceptance of intraocular lens implantation until that which has been obtained in recent years.

As noted, both anterior as well as posterior intraocular lenses have been implanted. The anterior chambers is more readily accessible and has been the position of choice in recent years. Lenses containing loops extending in both the posterior and anterior chambers of the lens and holding the lens at the pupil of the eye have, in the past, been widely used. However, erosion of the iris, due to the contact of the loops and the iris, has caused some difficulty with this type of lens.

Recently lenses have been utilized for implantation in the posterior chamber of the eye. Examples of such lenses are those disclosed in Kelman U.S. Pat. No. 4,092,743; Richards et. al. U.S. Pat. No. 4,014,049, Jensen U.S. Pat. No. 4,110,848, and Shearing U.S. Pat. No. 4,159,546. In the Kelman patent, lenses having three-point contact supporting means are disclosed. These lenses can contain metal wire loops in place of the illustrated solid support members of the patent. The lens can be placed in the posterior chamber of the eye as shown in FIG. 3 of Kelman. The lens is held in place by suturing of the lens to the iris.

In the Shearing patent, a posterior chamber lens is disclosed which has two J-shaped elastic support members which are resiliently compressed to allow for the lens to be placed within the posterior chamber of the eye. The lens in Shearing is to have primary ciliary body fixation, thus the J-shaped support members disclosed in the Shearing patent are of sufficient length and resiliency to provide such fixation. However, the J-shaped support members, because of their J shape, do not have substantial resistance to torsional twisting and flexing and it is consequently difficult to accurately and predictably position the lens and its support members in the posterior chamber.

Positioning of a lens having a configuration similar to that of FIG. 9 of the Shearing patent in the lens capsule in the posterior chamber of the eye was proposed by Sheets prior to my invention of the lens herein described.

While the development of intraocular lenses has proceeded to a level of increased sophistication since the implantation of the Ridley lens, a lens for the posterior chamber, preferably the lens capsule, which is easy to implant yet has stability without suturing has, prior to the present invention, been unknown. The present invention involves an intraocular lens for positioning in the posterior chamber of the eye, preferably the lens capsule of the eye, comprising a lens body, first and second support members extending from the lens body for engaging the outer portion of the posterior chamber of the eye, at least one of said support members comprising a resilient spring-like support loop extending outwardly from the periphery of said lens body, said support loop having first and second end portions attached to the lens body at first and second attachment locations and being dimensioned and shaped to engage the outer portion of the posterior chamber of the eye with an outward radial force when positioned therein so that the outer contact portion of said resilient loop is deflected inwardly from the normal relaxed position by the outer portion of the posterior chamber of the eye to provide the support for the lens body in the posterior chamber.

The lens is designed for easy and essentially automatic and accurate positioning within the posterior chamber, preferably the lens capsule of the eye. The lens is vertically, horizontally and rotationally secured by the spring action of the support loops in contact with the interior surface of the outer portion of the posterior chamber of the eye. Preferably, the lens is placed in the lens capsule. There is normally no need for suturing of the support means to any portion of the eye and when the lens is placed in the natural lens capsule there is ordinarily an absence of contact with the ciliary body. If the lens is placed in the lens capsule and there is an attendant absence of contact with the ciliary body, problems which can be caused by contacting the blood carrying vessels of the ciliary body of the eye are reduced. Since the support loop is connected to the lens body on both ends thereof, the lens can be positioned with a minimum possibility of rotational or torsional movement of the lens body in the eye.

The invention will now be described in more detail with reference to the following drawings in which FIG. 1 is a front elevation view of the preferred embodiment of the invention.

FIG. 2 is a side elevation view of the preferred embodiment.

FIG. 3 is a front elevation view of the preferred embodiment as implanted in the eye, less portions removed for clarity, and FIG. 4 is a sectional view of the eye of FIG. 3 with the lens in the implanted position.

Referring now to FIGS. 1 and 2, the preferred embodiment of the intraocular lens of the present invention 1 comprises a lens body 2. The lens body is normally four to six millimeters in diameter and is made by molding or lathing of optical polymeric material such as polymethyl methacrylate. Lens body 2 contains cylindrical surface 3, planar posterior surface 4, and spherical anterior surface 5. The spherical anterior surface 5 is of a desired curvature to give the required optical characteristics which are necessary for the patient in which the lens is implanted.

The lens body is held in place in the eye by means of support loops 6 and 7. These support loops are made of a resilient spring-like material. Normally the material is of a circular configuration and is comprised of polypropylene. Other materials having similar resiliency characteristics and having other cross sectional configurations can be used if they are inert and substantially non-reactive in the human body. The diameter of the loops is normally about 0.15 millimeter. Loops 6 and 7 are in a common plane with the lens body 2, are generally symmetrical with the optical as well as geometric axis 8 of the lens body 2 and are foot-shaped, the ankle portion thereof being attached to lens body 2. In the relaxed condition of the lens 1, as shown in FIG. 1, the outer periphery of loops 6 and 7 will generally be approximately twelve millimeters apart if the lens is to be placed in the lens capsule. If the lens is to be placed in the posterior chamber and not in the lens capsule the distance between the outer periphery of loops 6 and 7 will normally be about 13 millimeters. Loops 6 and 7 are of an identical configuration. As shown and preferably, loops 6 and 7 extend beyond lens body 2 in that each loop extends past a line tangent to cylindrical surface 3 of lens body 2 and parallel to a vertical line drawn through geometric axis 8 of lens body 2. Each loop contains a first end portion 9 attached to lens body 2 and leading to a curved leg 10 leading to curved portion 11 which is to contact the outer portion of the posterior chamber of the eye or preferably the equator of the lens capsule of the eye. Curved contact portion 11 is in turn connected to a second leg 12 which forms a smooth S curve back to the lens body 2. Second leg 12 is attached to lens body 2 at second end portion 13. First and second end portions 9 and 13 are respectively attached to the lens body 2 at holes 14 and 15 in lens body 2. The end portions 9 and 13 are radially positioned inside the lens body 2 and are normally bonded in holes 14 and 15 by heat probe, ultrasonic probe, or adhesive in a conventional manner. Lens body 2 and loops 6 and 7 can also be molded unitarily.

The curved contact portion 11 of loops 6 and 7 is designed to have a curve which is substantially equivalent to that of the outer portion of the posterior chamber of the eye or preferably the equator of the lens capsule so that when the loops 6 and 7 are compressed within the posterior chamber or lens capsule the curved portion 11 of loops 6 and 7 follow outer portion of the posterior chamber or the equator of the lens capsule. Since the posterior chamber and lens capsule vary from one patient to the other, often this curve will not track that of the posterior chamber or equator. In some cases, only a portion of the curved contact portion 11 will contact the posterior chamber outer portion or equator of the lens capsule. Additionally, in some cases the lens may be improperly placed in the lens capsule so that one support loop is in the lens capsule while the other is not.

The support loops 6 and 7 contain first and second end portions 9 and 13 with legs 10 and 12 which diverge outwardly from lens body 2 to curved portion 11. The leg 10 is a smooth curve less than 180 degrees while leg 12 is an S configuration having two curved portions oppositely oriented, the first of which and closest to the curved portion 11 is approximately 180 degrees in curvature while the second portion is less than 180 degrees in curvature.

In use the intraocular lens 1 is preferably placed within the eye after the natural lens has been removed from the lens capsule by normal extracapsular cataract removal. Referring to FIGS. 3 and 4, the central portion 16 of the lens capsule interior surface is removed along with the natural lens. This leaves the equatorial region 17 and posterior wall 18 of the lens capsule in the position shown in FIG. 4.

The lens 1 is positioned within the lens capsule 19 by compression of loops 6 and 7. This compression causes loops 6 and 7 to move cylindrically around the lens body 2 and towards the lens body 2. Leg 12 and curved portion 11 of loops 6 and 7 become closer in proximity during the compression and leg 10 is deflected. Support loops 6 and 7 are held against equator 17 of the lens capsule 19. The lens body is positioned so that it does not contact iris 20 of the eye and loops 6 and 7 are preferably positioned so they do not in the normal positioning contact the ciliary body 21 of the eye which contains blood vessels which are subject to rupture. The lens body 2 is held in place by support loops 6 and 7 without the need for additional sutures by means of the outward radial force applied by loops 6 and 7 at curved contact portion 11 against the equator 17 of lens capsule 19. Lens body 2 resides behind iris 20 and cornea 22.

It should be understood that the spirit and scope of the invention is not limited to the preferred embodiment. Modifications of the preferred embodiment will occur to those skilled in the art and are included within the following claims.

What is claimed is:

1. An intraocular lens for positioning in the posterior chamber of the eye comprising a lens body, first and second support members extending from the lens body for engaging the outer portion of the posterior chamber of the eye, at least one of said support members comprising a resilient spring-like support loop extending outwardly from the periphery of said lens body, said support loop being foot-shaped with the ankle portion of the foot being attached to the lens body, said support loop having first and second end portions attached to the lens body at first and second attachment locations and said support loop being shaped to provide an outer contact portion extending a substantial distance outwardly beyond adjacent portions of the support loop, said outer contact portion being dimensioned and shaped to engage the outer portion of the posterior chamber of the eye with an outward radial force when positioned therein so that the outer contact portion of said resilient loop is deflected inwardly from the normal relaxed position by the outer portion of the posterior chamber of the eye to provide the support for the lens body in the posterior chamber.

2. The lens of claim 1 wherein said support loop includes a first support leg extending between the first end portion and the outer contact portion.

3. The lens of claim 2 wherein said support loop includes a second support leg extending between the second end portion and the outer contact portion.

4. The lens of claim 3 wherein the first and second end portions of said support loop extend inwardly from the peripheral edge of the lens body.

5. The lens of claim 4 wherein the first support leg is curved, said outer contact portion is curved, and said second support leg is curved.

6. The lens of claim 5 wherein said first and second support legs of said loop outwardly diverge from said first and second end portions.

7. The lens of claim 1 wherein said support loop has sufficient resiliency such that when said support loop is compressed it moves cylindrically around said lens body and towards said lens body.

8. The lens of claim 1 in which each of said first and second support members comprise a resilient spring-like support loop extending outwardly from the periphery of said lens body, each of said support loops being foot-shaped with the ankle portion of the foot being attached to the lens body, each said support loops having first and second end portions attached to the lens body at first and second attachment locations and each of said support loops being shaped to provide an outer contact portion extending a substantial distance outwardly beyond adjacent portions of the support loop, said outer contact portion being dimensioned and shaped to engage the outer portion of the posterior chamber of the eye with an outward radial force when positioned therein so that the outer contact portion of said resilient loops is deflected inwardly from the normal relaxed position by the outer portion of the posterior chamber of the eye to provide the support for the lens body in the posterior chamber.

9. The lens of claim 8 wherein each said support loop includes a first support leg extending between the first end portion and the outer contact portion and a second support leg extending between the second end portion and the outer contact portion.

10. The lens of claim 9 wherein the first and second end portions of each of said support loops extend inwardly from the peripheral edge of the lens body and said first and second support legs of each of said loops outwardly diverge from said first and second end portions.

11. The lens of claim 10 wherein in each support loop the first support leg is curved, the outer contact portion is curved, and the second support leg is curved.

12. The lens of claim 11 wherein said support loops are oppositely disposed on lens body and oriented cylindrically in a like manner.

13. An intraocular lens for positioning in the lens capsule of the eye comprising a lens body, first and second support members extending from the lens body for engaging the lens capsule, at least one of said support members comprising a resilient spring-like support loop extending outwardly from the periphery of said lens body, said support loop being foot-shaped with the ankle portion of the foot being attached to the lens body, said support loop having first and second end portions attached to the lens body at first and second attachment locations and said support loop being shaped to provide an outer contact portion extending a substantial distance outwardly beyond adjacent portions of the support loop, said outer contact portion being dimensioned and shaped to engage the outer equatorial area of the lens capsule with an outward radial force when positioned therein so that the outer contact portion of said resilient loop is deflected inwardly from the normal relaxed position by the lens capsule to provide the support for the lens body in the lens capsule.

14. The lens of claim 13 wherein each of said support loops includes a first support leg extending between the first end portion and the outer contact portion.

15. The lens of claim 14 wherein said support loop includes a second support leg extending between the second end portion and the outer contact portion.

16. The lens of claim 15 wherein the first and second end portions of said support loop extend inwardly from the peripheral edge of the lens body.

17. The lens of claim 16 wherein the first support leg is curved, said outer contact portion is curved, and said second support leg is curved.

18. The lens of claim 17 wherein said first and second support legs of said loop outwardly diverge from said first and second end portions.

19. The lens of claim 13 wherein said support loop has sufficient resiliency such that when said support loop is compressed it moves cylindrically around said lens body and towards said lens body.

20. The lens of claim 13 in which each of said first and second support members comprise a resilient spring-like support loop extending outwardly from the periphery of said lens body, each of said support loops being foot-shaped with the ankle portion of the foot being attached to the lens body, each said support loop having first and second end portions attached to the lens body at first and second attachment locations and each of said support loops being shaped to provide an outer contact portion extending a substantial distance outwardly beyond adjacent portions of the support loop, said outer contact portion being dimensioned and shaped to engage the outer equatorial region of the lens capsule with an outward radial force when positioned therein so that the outer contact portion of said resilient loops is deflected inwardly from the normal relaxed position by the lens capsule to provide the support for the lens body in the lens capsule.

21. The lens of claim 20 wherein each said support loop includes a first support leg extending between the first end portion and the outer contact portion and a second support leg extending between the second end portion and the outer contact portion.

22. The lens of claim 21 wherein the first and second end portions of each of said support loops extend inwardly from the peripheral edge of the lens body and said first and second support legs of each of said loops outwardly diverge from said first and second end portions.

23. The lens of claim 22 wherein in each support loop the first support leg is curved, the outer contact portion is curved, and the second support leg is curved.

24. The lens of claim 23 wherein said support loops are oppositely disposed on said lens body and oriented cylindrically in a like manner.

* * * * *